US007833797B2

(12) United States Patent
Pal et al.

(10) Patent No.: US 7,833,797 B2
(45) Date of Patent: Nov. 16, 2010

(54) METHOD OF STAINING PROTEINS USING ALTA

(75) Inventors: Jayanta K. Pal, Pune (IN); Dhanashri Godbole, Pune (IN); Kiran Sharma, Pune (IN)

(73) Assignee: Council of Scientific & Industrial Research (IN)

( * ) Notice: Subject to any disclaimer, the term of this patent is extended or adjusted under 35 U.S.C. 154(b) by 522 days.

(21) Appl. No.: 11/216,947

(22) Filed: Aug. 31, 2005

(65) Prior Publication Data

US 2006/0073602 A1 Apr. 6, 2006

Related U.S. Application Data

(60) Provisional application No. 60/606,545, filed on Sep. 1, 2004.

(51) Int. Cl.
*G01N 33/00* (2006.01)
(52) U.S. Cl. .................... 436/86; 436/88; 436/164; 436/166; 436/169; 436/174; 436/179; 8/636; 8/657; 8/658
(58) Field of Classification Search .................. 436/86, 436/88, 164, 166, 169, 174, 179; 8/636, 8/657, 658
See application file for complete search history.

(56) References Cited

U.S. PATENT DOCUMENTS

| 5,039,619 | A  | * | 8/1991 | Staple et al. ................. 436/164 |
| 6,555,116 | B1 | * | 4/2003 | Buchanan et al. ......... 424/275.1 |
| 2003/0013208 | A1 | * | 1/2003 | Jendoubi ..................... 436/518 |

OTHER PUBLICATIONS

Bajaj, A. K., et al., Contact Depigmentation Caused by an Azo Dye in Alta, 1998, Contact Dermatitis, 38, 189.*
Instructions GelCodeTM Blue Safe Protein Stain [online] Thermo Scientific [retrieved on May 20, 2008] Retrieved from the internet <URL: http://www.piercenet.com/files/1995as4.pdf>.*
Thermo Scientific, Instructions "GelCode Blue Safe Protein Stain," 1995, pp. 1-3.
Bajaj et al.; "Contact depigmentation caused by an azo dye in alta," Contact Dermatitis, 1998, 38, pp. 189-193.
Jung et al.; "Mixed-dye staining method for protein detection in polyacrylamide gel electrophoresis using calconcarboxylic acid and rhodamine B," Electrophoresis (19(14), 1998 hardcopy, available online Apr. 14, 2005, pp. 2412-2415.
Choi et al.; "Fast Protein Staining in Sodium Dodecyl Sulfate Polyacrylamide Gel using Counter ion-Dyes, Coomassie Brilliant Blue R-250 and Neutral Red," Arch Pharm Res vol. 25, No. 5, pp. 704-708, 2002.

* cited by examiner

*Primary Examiner*—Yelena G Gakh
*Assistant Examiner*—Robert Xu
(74) *Attorney, Agent, or Firm*—Cantor Colburn LLP

(57) ABSTRACT

The present invention relates to a method of staining proteins in gels and membranes using stain alta.

12 Claims, 5 Drawing Sheets

[A]

[B]

1 2 3 4 5 6 7 8 9 10        1 2 3 4 5 6 7 8 9 10        2 3 4 5 6 7 8 9 10

METHOD OF STAINING PROTEINS USING ALTA

CROSS REFERENCE TO RELATED APPLICATIONS

This application claims the benefit of U.S. Provisional Application No. 60/606,545, filed Sep. 1, 2004, which is incorporated herein by reference in its entirety.

FIELD OF INVENTION

The present invention relates to a method of staining proteins using ALTA.

BACKGROUND AND PRIOR ART OF THE INVENTION

Sodium dodecyl sulfate polyacrylamide gel electrophoresis (SDS-PAGE) is one of the widely used methods for analysis and characterization of proteins in life science research. Realizing its importance and various applications, due efforts are continuously being made to improve on this method. Among various parameters, detection of protein bands following electrophoretic separation has drawn a great deal of attention. Generally, visualization of protein bands involves staining of the proteins by protein-specific stains followed by destaining of the gels to obtain a clear background. For example, the standard Coomassie Brilliant Blue (CBB)-staining procedure involves immersing the gel in a solution of methanol/acetic acid/water containing 0.1% CBB R-250 followed by destaining with the same solution without the stain. Although various methods of staining and destaining of proteins on gels have been described, a continuous update on the use of new stains and procedures are appreciated by researchers in this field.

SUMMARY OF THE INVENTION

Accordingly, the present invention discloses the use of a pre-existing scarlet red stain of cosmetic use, called ALTA, for staining SDS polyacrylamide gels and nitrocellulose membranes. This stain is easy to use, inexpensive (requires only 10% solution of ALTA) and the destaining procedure requires only low concentration of acetic acid as compared to the conventional de-stainer containing methanol/acetic acid/water. Further, for Western blot analysis, addition of 5% ALTA in the top tank buffer is enough to monitor the protein profile on the gel, as well as on the nitrocellulose membrane after electrotransfer, simply by viewing fluorescence on a UV-transilluminator. This method thus eliminates the need to run separate gels for protein staining on gel and for Western blot analysis, thereby reducing the time and expense for Western blot analysis.

OBJECTS OF THE INVENTION

The primary aim of the present invention is to describe a new stain or a new method or a modification of the existing methods, keeping in mind of the following three criteria sensitivity of the stain, simple ness of the procedure and the expense.

DETAILED DESCRIPTION OF THE INVENTION

Accordingly the present invention provides a method of staining proteins using ALTA.

One embodiment of the present invention relates to a method of staining proteins using stain ALTA, said method comprising the steps of exposing the proteins to ALTA in gels and/or membranes, de-staining the gels of step and obtaining stained proteins.

In another embodiment of the invention, the membranes are nitrocellulose membranes.

In another embodiment of the invention, the staining in gels is done in Electrophoresis.

In another embodiment of the invention, the gels are sodium dodecyl sulfate (SDS) polyacrylamide gels.

In yet another embodiment of the invention, the amount of ALTA used in the staining is in the range of 5-15%.

In yet another embodiment of the invention, the preferred amount of ALTA used in staining is 10%.

In yet another embodiment of the invention, the gels are stained with a solution consisting ALTA, methanol, and acetic acid in the proportion of 3-5:4-6:0-2 for 1-3 h.

In still another embodiment of the invention, the gels are stained with a solution consisting ALTA, methanol, and acetic acid in the proportion of 4:5:1 for 3 h.

In still another embodiment of the invention, the gels are de-stained with acetic acid of concentration ranging between 5-9% for the time duration ranging in between 18-22 h.

In still another embodiment of the invention the gels are de-stained with about 7% acetic acid for about 20 h.

In a another embodiment of the invention, the proteins are in Western Blot Analysis In another embodiment of the invention, ALTA is added in the top tank buffer in Western Blot Analysis.

In another embodiment of the invention, ALTA added in the top tank is in the range of between 3-8%.

In another embodiment of the invention, ALTA added in the top tank is about 5%.

In a further embodiment of the invention the invention relates to a kit comprising providing the means for storing the proteins to be stained, providing the contacting means for staining the protein with ALTA.

In another embodiment of the invention, the amount of ALTA used in the staining is in the range of 5-15%.

In another embodiment of the invention, the preferred amount of ALTA used in the staining is in the range of 10%.

In still another embodiment of the invention, the proteins are stained with a solution consisting ALTA, methanol, acetic acid in the proportion of 3-5:4-6:0-2 for 1-3 h.

In still another embodiment of the invention, the proteins are stained with a solution consisting ALTA, methanol, acetic acid in the proportion of 4:5:1 for 3 h.

Figure 1:
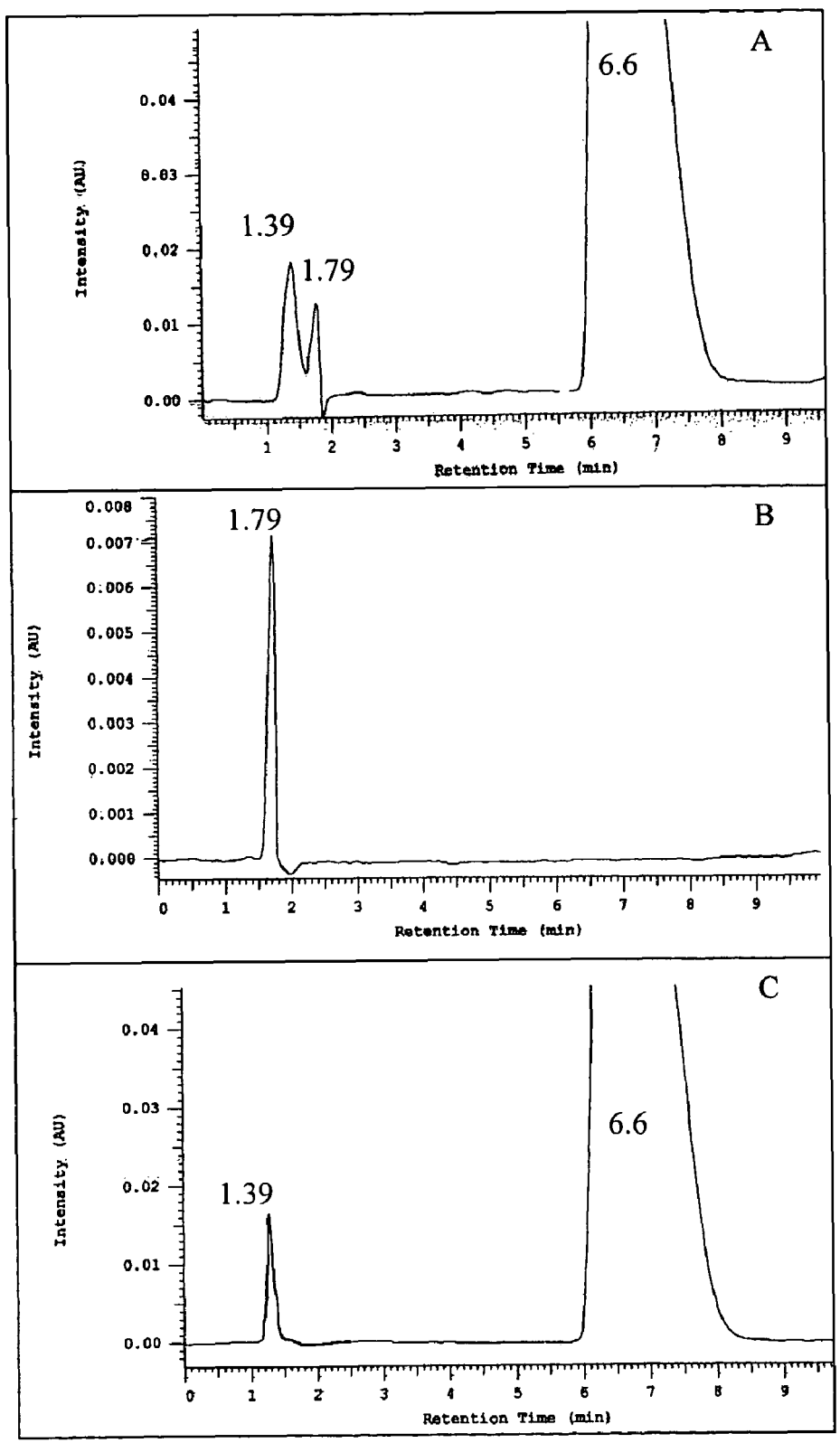
FIG. 1 HPLC chromatograms of ALTA and its comparison with those of Crocein scarlet and Rhodamine B. (A) 1:15 diluted ALTA, (B) 0.24 mg/ml Rhodamine B and (C) 0.56 mg/ml Crocein scarlet.

The invention is further extrapolated with the help of following examples. However, this should not be considered to limit the scope of the invention.

EXAMPLES

Example 1

Analysis of Composition of Alta by HPLC

HPLC analysis of ALTA was carried out using MERCK-HITACHI HPLC system in combination with photodiode array detector (MERCK-HITACHI L-7455) with a wavelength range from 180 to 800 nm. The samples were analysed using C-18 (Nucleosil) column (12.5 cm) at 25° C. The solvent used for eluting the samples was 1 mM ammonium acetate in methanol and water (1:1, v/v). The flow rate was set at 0.6 ml/min in isocratic condition. The detection wavelength was set from 250 to 650 nm and absorbances of the samples were monitored at 285 nm. All the systems were interfaced to a computer and the raw data were analysed by using the software Multi-HSM-D7000.

Example 2

Protein Extraction and Estimation of Protein Concentrations

Protein samples used in these experiments were from four sources, namely, in vitro cultured mouse melanoma cells (B16F10), human K562 cells, 19-day-old chick embryo liver and chickpea. Proteins were extracted in the lysis buffer containing the following: 20 mM Tris-HCl, pH 8.0, 1 mM EDTA, 1 mM PMSF, protease inhibitor cocktail (Boehringer Mannheim, Germany) and 0.1% Triton X-100. Protein extracts were centrifuged at 15,000 rpm for 20 min and the soluble supernatants were used for analysis. Protein concentrations in the samples were estimated by the micro method of Bradford BSA was used as the standard protein.

Example 3

SDS-PAGE and Protein Staining

Samples containing 20, 30 and 50 μg proteins were subjected to SDS-PAGE (10% gel) according to Laemmli. The following proteins were used as the molecular weight marker proteins: myosin (205 kDa), phosphorylase b (97 kDa), bovine serum albumin (66 kDa), ovalbumin (43 kDa) and carbonic anhydrase (29 kDa). Electrophoresis of proteins in two identical gels was carried out at a constant current of 20 mA for 1 h. Staining and destaining of one gel was carried out by the standard CBB staining procedure [staining in 0.1% CBB R-250 dissolved in methanol/acetic acid/water (5:1:4) for 2 h followed by destaining in the same solution without the stain for 10-12 h]. While the other gel was stained in ALTA solution mixed with methanol and acetic acid (4:5:1) for 2 h, and de-stained in 7% acetic acid for 20 h. In separate experiments, gels were also stained with a mixture of 0.8% Crocein scarlet (brilliant crocein) and 0.2% Rhodamine B, prepared in 50% methanol and 10% acetic acid. These concentrations are chosen as per their concentrations in ALTA solution, determined by HPLC analysis.

Example 4

Western Blot Analysis

Protein samples were analysed by SDS-PAGE as described above. ALTA stain was added in the top tank buffer to a final concentration of 5% v/v (0.4% Crocein scarlet and 0.1% Rhodamine B) before electrophoresis. Following the electrophoresis, the gel was viewed 100 on a UV-transilluminator and the protein profile was recorded on a gel documentation system (Bio-Rad, USA). Thereafter, the gel was transferred in a wet electrotransfer system (70 mA, 16 h), according to Towbin et al. Following transfer, the nitrocellulose membrane was viewed on a UV-transilluminator, profile recorded and processed further for immunoreaction as follows. The membrane was saturated with 3% BSA for 4 h, reacted with anti-HSP70 mouse monoclonal antibody, followed by anti-mouse IgG-alkaline phosphatase as the secondary antibody. The blot was developed using BCIP and NBT as the substrates and the results photographed.

Example 5

Chemical Composition of Alta Determined by HPLC Analysis

The HPLC chromatogram of 1:15 diluted ALTA solution showed three distinct peaks with retention times 1.39, 1.79 and 6.6 min (FIG. 1A). These peaks correspond to the retention time of 1.79 min of Rhodamine B (0.24 mg/ml) and with retention time of 1.39 and 6.6 min of Crocein scarlet (0.56 mg/ml) as seen in FIGS. 1B and C, respectively. The results indicated that the spectra of the peaks of ALTA were identical to those of Rhodamine B (1.79 min) and those of Crocein scarlet (1.39 and 6.6 min) suggesting that Crocein scarlet and Rhodamine B are the constituents of ALTA. Similar chemical composition of ALTA has been reported earlier Spiking was carried out using the standards, Rhodamine B and Crocein scarlet, to further confirm the composition of ALTA. The HPLC chromatogram of spiked ALTA with each of the standards showed an increase in intensity of the respective peaks proportionally with the concentration of the standards added, thereby confirming that ALTA consists of two dyes, Crocein scarlet and Rhodamine B. Further, the concentrations of Crocein scarlet and Rhodamine B in ALTA are 8 and 2 mg/ml, respectively, as calculated from the areas of the peaks.

Example 6

Protein Profile Stained by Alta and its Comparison with that Stained by CBB-250

Figure 2:
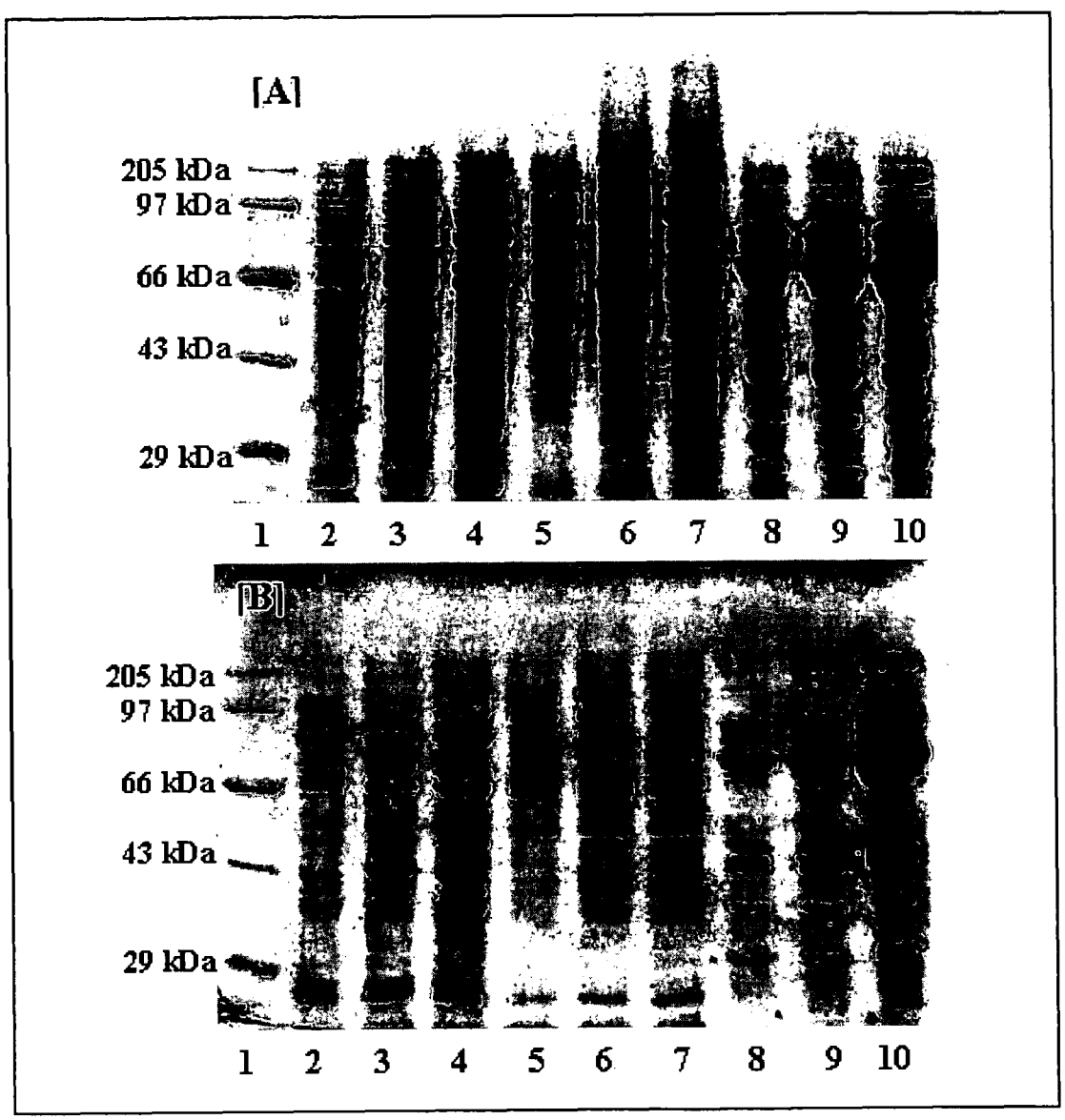
FIG. 2 SDS-PAGE profiles of water-soluble proteins stained by CBB R-250 (A) and ALTA (B). Protein extracts from mouse melanoma cells (lanes 2-4), 19-day-old chick liver (lanes 5-7) and chickpea (lanes 8-10) were electrophoresed on two identical SDS polyacrylamide gels (10%). The 20 µg (lanes 2, 5, 8), 30 µg (lanes 3, 6, 9) and 50 µg (lanes 4, 7, 10) proteins were loaded; lane 1, molecular weight marker proteins. Staining and destaining were done as described in the text.
Figure 3:
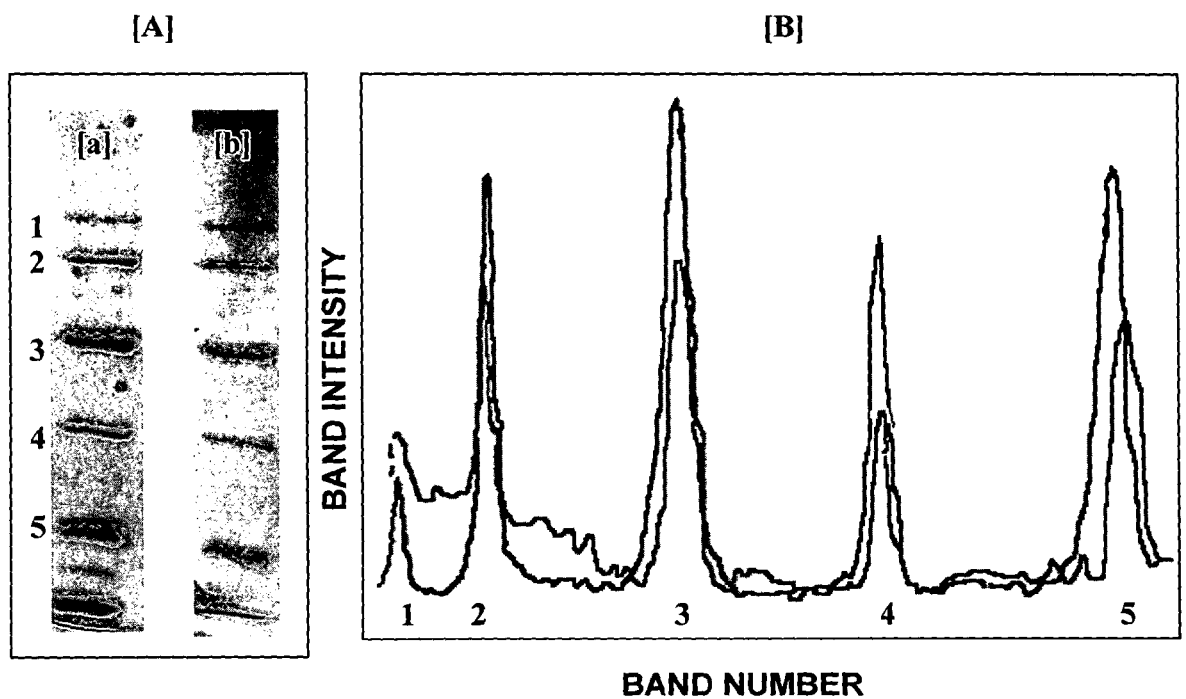
FIG. 3 Scan profiles (B) of the molecular weight marker proteins resolved on the SDS gel shown in FIG. 2 (A). Molecular weight marker protein bands 1-5 (A) in both CBB- and ALTA-stained gels (a, b) were scanned in a Bio-Rad gel documentation system and the profiles are represented (B) as blue lines and red lines, respectively. Band_intensity is plotted as arbitrary units. (For interpretation of the references to colour in this figure legend, the reader is referred to the web version of this article).
Figure 4:
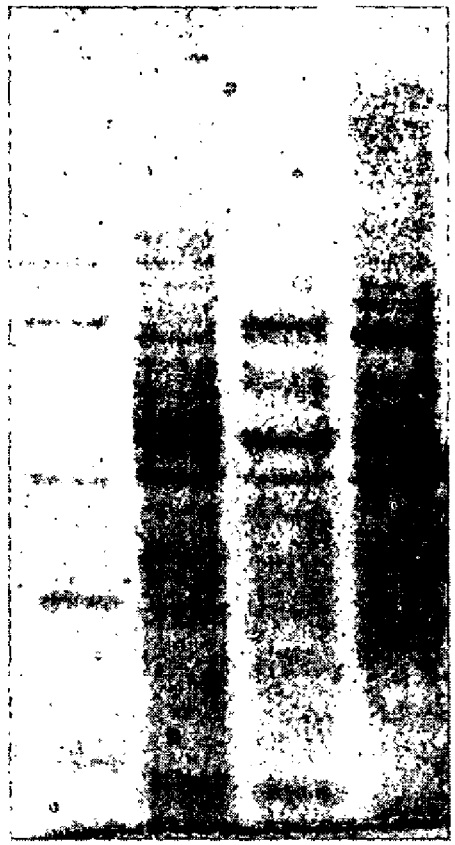
FIG. 4 SDS-PAGE profiles of water-soluble proteins stained by ALTA (A) and by a mixture of Crocein scarlet and Rhodamine B (B). Lane 1, molecular weight marker proteins; lanes 2-4, 30 μg protein extract of K562, B16 mouse melanoma cells and chick liver, respectively.
Figure 4:
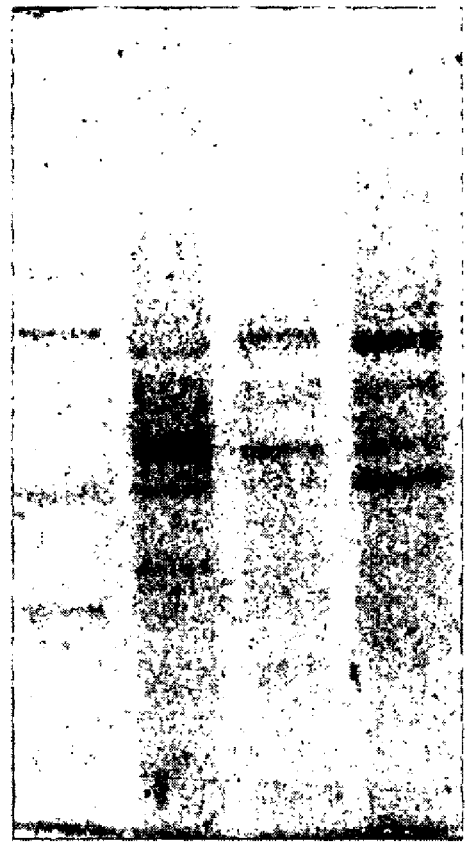

The resolution of the protein samples in the gel stained by ALTA appeared similar to that stained by CBB (FIGS. 2A,B). The resolution remained unaffected irrespective of the type of protein samples used, including the standard molecular weight marker proteins. Further, the binding of the stain ALTA to protein bands appeared to increase as a function of protein concentration, as was observed in case of the CBB stain. However, destaining of the ALTA-stained gel by the standard destaining procedure used for CBB-stained gel led to a significant loss of staining of the protein bands. Interestingly, destaining with 7% acetic acid alone was much more effective. Similar results were obtained for the total tissue/cell extracts (FIG. 2; data on scanning) When the cost of these two staining procedures was estimated, ALTA-staining was found to be about three-times cheaper as compared to the CBB-staining procedure. It was observed that this procedure is equally efficient for non-denaturing polyacrylamide gels. After having identified the components of ALTA, the staining gels was done with a mixture of 0.8% (w/v) Crocein scarlet and 0.2% (w/v) Rhodamine B prepared in methanol/acetic acid/water (50:10:40). Upon comparison, it was observed that the protein profile obtained with this solution was identical to that obtained by ALTA (FIG. 4).

These results together further confirm the composition of ALTA, and also indicate that these components in a proportion of 80:20 may be universally used as an alternative procedure for protein staining.

Figure 5:
FIG. 5 One step staining of proteins on gel (A) and on Nitrocellulose membrane (B) by ALTA during Western blot analysis, and Western blot signal (C) on the ALTA-stained membrane. (A) ALTA-stained polyacrylamide gel as observed under UV-transilluminator. The 5% ALTA was incorporated in the upper tank buffer when the protein samples were electrophoresed. (B) ALTA-stained proteins transferred on nitrocellulose membrane as seen under UV-transilluminator. (C) Western blot signal of HSP70 on ALTA-stained membrane using anti-HSP70 antibody. Lane 1, molecular weight marker proteins; lanes 2-4, K562 cell extract; lanes 5-7, B16 melanoma cell extract; lanes 8-10, Chick liver extract. In each set 20, 30 and 40 μg proteins were loaded.
Figure 5:
Figure 5:

Use of Alta for Monitoring Protein Profile on Gel and on Nitrocellulose Membrane During Western Blot Analysis ALTA can also be used at a much lower concentration (5% v/v; half the concentration required for direct ALTA staining on gel) for Western blot analysis. Since one of the components of ALTA (Rhodamine B) is a chromofluor, the protein profile can be continuously monitored simply by viewing under a UV-transilluminator, at each step during the process, namely, after electrophoresis (FIG. 5A) and after electrotransfer on nitrocellulose membrane (FIG. 5B). The protein bands (red coloured due to Crocein scarlet) can be better observed against a fluorescent background (Rhodamine B). Further, this nitro-cellulose membrane can be processed further for immunoreaction leading to development of signal without any interference by the background stain (FIG. 5C); the background stain fades during the process of Western blot.

ADVANTAGES OF THE PRESENT INVENTION (1) Since no organic solvent is used, no interference of antigen-antibody interactions, thereby any compromise in the intensity of signal in the Western blot was observed.

(2) Since the stain is retained on the nitrocellulose membrane after transfer, monitoring of protein transfer by Ponceau Red S staining becomes redundant.

(3) Due to non-requirement of a few steps, the entire procedure is simple and short, and time-saving.

(4) The cost of individual experiments is reduced substantially as it eliminates the need to run two separate gels, one for staining and the other for Western blot, as done in the conventional approach. Our results thus suggest that this newly described staining procedure could be used as an alternative to the existing staining procedures including CBB-staining. This stain is highly inexpensive, available in the form of a ready-to-use stain, and thus may find its application in the area of protein electrophoresis and Western blot analysis.

We claim:

1. A method of staining proteins using stain ALTA, the method comprising the steps of:
   (a) exposing the proteins to ALTA in a top tank buffer in Western Blot Analysis to stain the proteins in gels and/or membranes;
   (b) de-staining the gels and/or membranes of step (a)
   (c) obtaining stained proteins.

2. A method as claimed in claim 1 wherein the membranes are nitrocellulose membranes.

3. A method as claimed in claim 1, wherein the staining in gels is done in Electrophoresis.

4. A method as claimed in claim 1, wherein the gels are sodium dodecyl sulfate (SDS) polyacrylamide gels.

5. A method as claimed in claim 4, wherein the amount of ALTA used in the staining is in the range of 5-15%.

6. A method as claimed in claim 5, wherein the amount of ALTA used in staining is 10%.

7. A method as claimed in claim 4, wherein the gels are stained with a solution consisting ALTA, methanol, acetic acid in the proportion of 3-5:4-6:0-2 for 1-3 h.

8. A method as claimed in claim 7, wherein the gels are stained with a solution consisting ALTA, methanol, acetic acid in the proportion of 4:5:1 for 3 h.

9. A method as claimed in claim 1, wherein the gels are de-stained with acetic acid of concentration ranging between 5-9% for the time duration ranging in between 18-22 h.

10. A method as claimed in claim 8, wherein the gels are de-stained with about 7% acetic acid for about 20 h.

11. A method as claimed in claim 1, wherein ALTA added in the top tank is in the range of between 3-8%.

12. A method as claimed in claim 11, wherein ALTA added in the top tank is about 5%.

* * * * *